United States Patent [19]

Spang et al.

[11] Patent Number: 5,047,539

[45] Date of Patent: Sep. 10, 1991

[54] HETEROCYCLIC AMIDINE DERIVATIVES

[75] Inventors: Peter Spang, Ingbert; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 511,302

[22] Filed: Apr. 19, 1990

[30] Foreign Application Priority Data

May 20, 1989 [DE] Fed. Rep. of Germany ....... 3916494

[51] Int. Cl.$^5$ .................. C07D 219/08; C07D 209/82
[52] U.S. Cl. ..................................... 546/164; 548/491; 548/449; 548/444; 524/94; 524/87; 546/101
[58] Field of Search ................ 546/164; 548/491, 444

[56] References Cited

U.S. PATENT DOCUMENTS 3,637,745 1/1972 Heller et al. ...................... 548/491
3,823,136 7/1974 Wu et al. ........................... 548/491
4,021,471 5/1977 Virgilio et al. ..................... 524/195

Primary Examiner—David B. Springer
Attorney, Agent, or Firm—Oblon, Spivak, McClelland, Maier & Neustadt

[57] ABSTRACT

Heterocyclic amidine derivatives of the general formula I

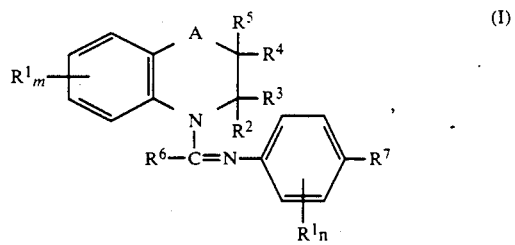

in which the variables $R^1$ are the same or different and denote hydrogen, $C_1$-$C_4$-alkyl, $C_1$-$C_4$-alkoxy, hydroxyl or chlorine, $R^2$ to $R^5$ denote hydrogen or $C_1$-$C_4$-alkyl and $R^3$ and $R^4$ can together form a five-membered or six-membered ring, $R^6$ denotes hydrogen or $C_1$-$C_8$-alkyl, $R^7$ denotes cyano or —COOR$^8$, —COR$^8$, —CONHR$^8$ or —CONR$^8{}_2$, in which $R^8$ is a straight-chain or branched-chain $C_1$-$C_{12}$-alkyl group which may be interrupted by oxygen atoms, a cyclopentyl or cyclohexyl group or a phenylalkyl group having from 1 to 3 carbon atoms in the alkyl moiety, A is a chemical bond or a methylene group which may additionally carry one or two $C_1$-$C_4$-alkyl radicals, and m and n are each 1 or 2.

The said heterocyclic amidine derivatives I serve as UV stabilizers for organic materials.

2 Claims, No Drawings

HETEROCYCLIC AMIDINE DERIVATIVES

The present invention relates to novel heterocyclic amidine derivatives of the general formula I $$\text{(I)}$$

in which the variables $R^1$ are the same or different and denote hydrogen, $C_1$-$C_4$-alkyl, $C_1$-$C_4$-alkoxy, hydroxyl or chlorine, $R^2$ to $R^5$ denote hydrogen or $C_1$-$C_4$-alkyl and $R^3$ and $R^4$ can together form a five-membered or six-membered ring, $R^6$ denotes hydrogen or $C_1$-$C_8$-alkyl, $R^7$ denotes cyano or —$COOR^8$, —$COR^8$, —$CONHR^8$ or —$CONR^8{}_2$, in which $R^8$ is a straight-chain or branched-chain $C_1$-$C_{12}$-alkyl group which may be interrupted by oxygen atoms, a cyclopentyl or cyclohexyl group or a phenylalkyl group having from 1 to 3 carbon atoms in the alkyl moiety, A is a chemical bond or a methylene group which may additionally carry one or two $C_1$-$C_4$-alkyl radicals, and m and n are each 1 or 2.

The invention also relates to a process for the manufacture of the above compounds, to the use of said compounds as UV stabilizers for organic materials and to UV-stabilized organic materials containing said compounds.

U.S. Pat. No. 4,021,471 discloses open-chain form-amide derivatives having the following basic structure $$\text{Alk—OOC—}\langle\text{ring}\rangle\text{—N=CH—N(R)—}\langle\text{ring}\rangle$$

in which Alk denotes alkyl and R denotes alkyl or phenyl, as UV stabilizers for organic materials.

However, the absorption maxima of most of these compounds are in the range of 310 to 320 nm (UV-B range) and UV radiation having a wavelength above 360 nm is inadequately absorbed by these compounds, so that organic materials, e.g. plastics materials, containing these agents are virtually unprotected against impairment caused by light in this wavelength range (UV-A). Furthermore, the photostability of these compounds is unsatisfactory on exposure to light over a moderately long period.

It is thus an object of the present invention to provide UV stabilizers for organic materials, which show good compatibility with the materials to be stabilized and high long-term photostability and are highly efficient even at wavelengths beyond 360 nm.

Accordingly, we have found the heterocyclic amidine derivatives I defined above.

More specifically, $R^1$ preferably stands for hydrogen, $C_1$-$C_4$-alkyl or $C_1$-$C_4$-alkoxy and in particular for hydrogen, methyl or methoxy.

$R^2$ to $R^5$ denote hydrogen or $C_1$-$C_4$-alkyl, in particular methyl. In addition, $R^3$ and $R^4$ may advantageously be linked to form a five-membered or six-membered ring.

The meanings of $R^1$ to $R^5$ are the same in the heterocyclic amines III serving as starting materials $$\text{(III)}$$

of which the following compounds are to be particularly preferred with a view to the desired properties of compounds I:

indoline
2-methylindoline
3-methylindoline
4-methylindoline
7-methylindoline
2,3-dimethylindoline
3,3-dimethylindoline
2,5-dimethylindoline
2,7-dimethylindoline
2,3,3-trimethylindoline
2,3,7-trimethylindoline
2,2,3,3-tetramethylindoline
2,3,3-trimethyl-5-methoxyindoline
1,2,3,4-tetrahydroquinoline
1,2,3,4-tetrahydroquinaldine
3-methyl-1,2,3,4-tetrahydroquinoline
4-methyl-1,2,3,4-tetrahydroquinoline
5-methyl-1,2,3,4-tetrahydroquinoline
6-methyl-1,2,3,4-tetrahydroquinoline
7-methyl-1,2,3,4-tetrahydroquinoline
1,2,3,4,10,11-hexahydrocarbazole.

$R^6$ preferably denotes methyl, ethyl, n-propyl or isopropyl or, in particular, hydrogen.

$R^7$ preferably stands for a cyano group or the radical —$COOR^8$ $R^8$ preferably stands for a straight-chain or branched-chain $C_1$-$C_{12}$-alkyl group optionally interrupted by oxygen atoms. Preferred radicals $R^8$ are methyl, ethyl, propyl, n-butyl, i-butyl, s-butyl, t-butyl, n-pentyl, n-hexyl, n-heptyl, 2-ethylhexyl, n-octyl, n-nonyl, i-nonyl, n-decyl, n-dodecyl, 2-methoxyethyl, 2-ethoxyethyl, 2-butoxyethyl and the following groups:

—$CH_2CH_2OCH_2CH_2OC_2H_5$,
—$CH_2CH_2OCH_2CH_2OC_4H_9$,
—$CH_2CH_2OCH_2CH_2OCH_2CH_2OC_2H_5$,
—$CH_2CH_2OCH_2CH_2OCH_2CH_2OC_4H_9$,
—$CH_2CH_2OCH_2CH_2OCH_2CH_2OCH_2CH_2OC_2H_5$ and
—$CH_2CH_2OCH_2CH_2OCH_2CH_2OCH_2CH_2OC_4H_9$.

Particularly preferred compounds of formula I are those of the general formula Ia, in which A stands in particular for a chemical bond or a grouping having the structure —$CH_2$— or —$CH(CH_3)$—:

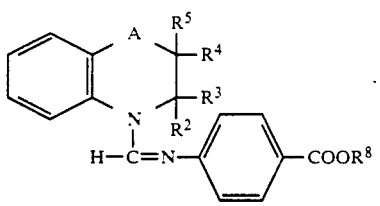

The heterocyclic amidine derivatives I of the invention are advantageously prepared by reacting an N-arylimidate of formula II

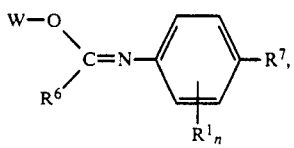

in which W stands for $C_1$-$C_4$-alkyl such as methyl, ethyl or propyl, with a heterocyclic amine III in known manner.

The N-arylimidates II may be prepared by conventional methods from, for example, the corresponding aniline derivatives V and trialkyl o-alkanoates.

In the event of $R^6$ standing for hydrogen, the heterocyclic amidine derivatives I of the invention may be advantageously prepared by reacting a heterocyclic N-formylamine IV

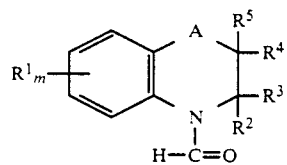

with an aniline derivative V

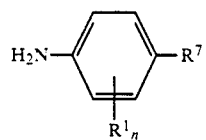

by conventional methods.

The N-formylamines IV may be readily prepared by conventional methods, for example by formylation of the heterocyclic amines III.

The derivatives of the general formula I and Ia in which $R^8$ denotes a higher alkyl radical optionally interrupted by oxygen atoms or denotes a phenylalkyl radical may be readily prepared in known manner by transesterification of the lower esters in which $R^8$ denotes, for example, methyl or ethyl.

The heterocyclic amidine derivatives I of the invention serve as UV stabilizers for organic materials, for example for cosmetic preparations, medical formulations and precursors of plastics materials and, in particular, for plastics materials per se.

Particularly suitable plastics materials are polyurethanes, polyesters, polyamides, polystyrene, acrylic acid/butadiene/styrene copolymers, hot-cross-linkable acrylic resins and thermoplastic acrylic resins. Also suitable are polyolefins, halogen-containing vinyl polymers, polyacrylates, polymethacrylates, polyacrylamides, polyacrylonitrile, polyvinylalcohol and acyl derivatives thereof, polyacetates, polyalkylene-oxides, polyphenylene-oxides, polyureas, polysulfones, polycarbonates, cross-linked polymers of aldehydes and phenols, urea or melamine, unsaturated polyester resins and alkyd resins.

The heterocyclic amidine derivatives I of the invention are particularly well-suited for stabilizing polyurethanes, and it is recommended that these agents be added to the polyurethane components prior to polymerization, i.e. to the polyol component or to the isocyanate component. When polyurethanes are stabilized in this way, they show not only good UV absorption but also improved thermal stability.

The invention also relates to UV-stabilized organic materials, particularly plastics materials, containing from 0.01% to 10% w/w and preferably from 0.1% to 5% w/w of one or more heterocyclic amidine derivatives I, based on the weight of the organic material.

The said organic materials may contain, in addition to compounds I, other auxiliaries and fillers in usual amounts, examples of which are:

other UV stabilizers such as 2-(2'-hydroxyphenyl)benztriazoles, 2,4-bis(2'-hydroxyphenyl)-6-alkyl-s-triazines, 2-hydroxybenzophenones or 1,3-bis(2'-hydroxybenzoyl)benzenes antioxidants based on phosphorus and sulfur compounds and on sterically hindered phenols and amines fillers such as lamp black, kaolin, talcum and glass fibers pigments such as titanium dioxide other auxiliaries such as plasticizers, lubricants, emulsifiers, optical brighteners, flame retardants and antistatic agents.

When said antioxidants are used, there may be significant increase in the stabilizing effect counteracting the action of light and, also, of elevated temperatures. Said agents or mixtures thereof are advantageously used in an amount of from 0.1 to 5%, and preferably from 0.5 to 3%, by weight of the organic material, together with the compound(s) I of the invention.

Examples of phosphorous antioxidants are tris(nonylphenyl) phosphite,
distearylpentaerithritol diphosphite
tris(2,4-di-t-butylphenyl) phosphite,
tris(2-t-butyl-4-methylphenyl) phosphite,
bis(2,4-di-t-butylphenyl)pentaerythritol diphosphite and
tetrakis(2,4-di-t-butylphenyl)-4,4'-biphenylene diphosphite.

Examples of sulfurous antioxidants are dilauryl thiodipropionate,
dimyristyl thiodipropionate,
distearyl thiodipropionate,
pentaerythritol tetrakis($\beta$-laurylthiopropionate) and
pentaerythritol tetrakis($\beta$-hexylthiopropionate).

Examples of suitable sterically hindered phenolic antioxidants are 2,6-di-t-butyl-4-methylphenyl, n-octadecyl-β-(3,5-di-t-butyl-4-hydroxyphenyl) propionate 1,1,3-tris(2-methyl-4-hydroxy-5-t-butylphenyl)butane, 1,3,5-trimethyl-2,4,6-tris(3,5-di-t-butyl-4-hydroxybenzyl)benzene, 1,3,5-tris(3,5-di-t-butyl-4-hydroxybenzyl) isocyanurate 1,3,5-tris[(3,5-di-t-butyl-4-hydroxyphenyl)propionyloxy-ethyl] isocyanurate, 1,3,5-tris(2,6-dimethyl-3-hydroxy-4-t-butylbenzyl) isocyanurate, pentaerythritol-tetrakis[β-(3,5-di-t-butyl-4-hydroxyphenyl)propionate] and tocopherol.

Examples of sterically hindered amines are bis(2,2,6,6-tetramethylpiperidyl) sebacate,
bis(1,2,2,6,6-pentamethylpiperidyl) sebacate,
the condensate of 1-hydroxyethyl-2,2,6,6-tetramethyl-4-hydroxypiperidine with succinic acid,
the condensate of N,N'-(2,2,6,6-tetramethylpiperidyl)-hexamethylenediamine with 4-t-octylamino-2,6-dichloro-1,3,5-s-triazine,
tris(2,2,6,6-tetramethylpiperidyl)nitrilo triacetate,
tetrakis(2,2,6,6-tetramethyl-4-piperidyl)1,2,3,4-butane-tetracarboxylic acid,
1,1'-(ethane-1,2-di-yl)-bis(3,3,5,5-tetramethylpiperazinone) and condensates of 4-amino-2,2,6,6-tetramethylpiperidines with tetramethylol-acetylene-diureas.

A particularly high degree of stabilization is achieved in polyurethanes when the latter are stabilized with a mixture of a heterocyclic amidine derivative I of the invention with a sterically hindered phenol or one of the aforementioned sulfurous or phosphorous compounds and a sterically hindered amine.

The heterocyclic amidine derivatives I of the invention are virtually colorless and usually show absorption maxima in the range of 320 to 350 nm and adequate extinction coefficients, so that light in the UV-A range, in particular light having a wavelength greater than 360 nm, is sufficiently absorbed by said compounds. Other advantages of the compounds I of the invention are their high degree of photostability when exposed to light over relatively long periods and their good compatibility with the organic materials, in particular plastics materials, to be stabilized.

EXAMPLES ILLUSTRATING THE PREPARATION OF AMIDINE DERIVATIVES Ia

EXAMPLES 1 to 3

Method (a)

0.25 mole of an N-arylformimidate II

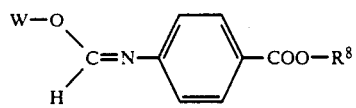

were reacted for t hours at T°C. with 0.27 mole of a heterocyclic amine III

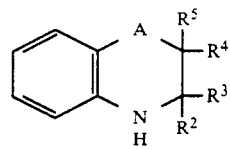

and the alcohol liberated was distilled off. The reaction product was cooled to approximately 80° C. and then caused to crystallize with p ml of methanol and then recrystallized from solvent S.

EXAMPLES 4 AND 5

Method (b)

0.25 mole of an N-formylamine IV

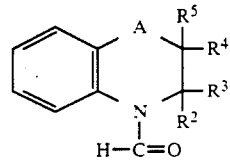

dissolved in 250 ml of chloroform was reacted in a first stage with 0.25 mole of phosphorus oxytrichloride for t hours at T°C. and in a second stage with 0.25 mole of an aniline derivative V

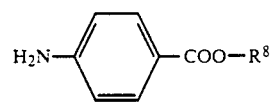

for t' hours at T'° C. After cooling, the reaction mixture was worked up by pouring it into a caustic soda/ice mixture, separating the phases, distilling off the chloroform and recrystallizing the product from solvent S.

EXAMPLES 6 TO 8

Method (c)

0.20 mole of the ethyl ester Ia obtained in Example 3, Example 1 and Example 5 respectively was stirred with 3 g of $Na_2CO_3$ and p ml of 2-ethylhexanol for t hours at T°C., while a stream of nitrogen was bubbled through the mixture. After cooling and filtering the mixture, the excess 2-ethylhexanol was filtered off in vacuo and the residue was taken up in ethyl acetate and treated with active carbon and fuller's earth. The mixture was then filtered and the solvent distilled off in vacuo to give, in each case, a pale yellow oil.

Data concerning the above Examples and the products obtained are listed in the Table below.

TABLE 1

Preparation of heterocyclic amidine derivatives Ia

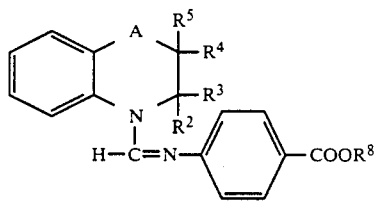

| Example No. | A | $R^2$ | $R^3$ | $R^4$ | $R^5$ | $R^8$ | W | T [°C.] | t [h] | T' [°C.] | t' [h] | p [ml] |
|---|---|---|---|---|---|---|---|---|---|---|---|---|
| Method (a) | | | | | | | | | | | | |
| 1 | — | H | H | H | H | $C_2H_5$ | $C_2H_5$ | 160 | 1.25 | | | 400 |
| 2 | $CH_2$ | H | H | H | H | $C_2H_5$ | $C_2H_5$ | 190 | 2 | | | 125 |
| 3 | — | $CH_3$ | H | H | H | $C_2H_5$ | $C_2H_5$ | 190 | 2 | | | 350 |
| Method (b) | | | | | | | | | | | | |
| 4 | — | $CH_3$ | H | H | H | $C_2H_5$ | | 40 | 0.25 | 60 | 2 | |
| 5 | — | H | —$(CH_2)_4$— | | H | $C_2H_5$ | | 40 | 2 | 60 | 2 | |
| Method (c) | | | | | | | | | | | | |
| 6 | — | $CH_3$ | H | H | H | 2-ethylhexyl | | 135 | 36 | | | 100 |
| 7 | — | H | H | H | H | 2-ethylhexyl | | 135 | 23 | | | 235 |
| 8 | — | H | —$(CH_2)_4$— | | H | 2-ethylhexyl | | 130 | 15 | | | 225 |

| Example No. | S | Yield [g] | m.p. [°C.] | UV Data $\lambda_{max}$ [nm] | $\epsilon(CH_2Cl_2)$ |
|---|---|---|---|---|---|
| Method (a) | | | | | |
| 1 | methanol | 45.9 | 101–102 | 338 | 31,000 |
| 2 | methanol | 66.5 | 119–120 | 326 | 32,000 |
| 3 | ethanol* | 58.8 | 103–105 | 338 | 31,600 |
| Method (b) | | | | | |
| 4 | ethanol* | 59.2 | as in Example 3 | | |
| 5 | $^1$EA* | 48.5 | 107–108 | 337 | 34,100 |
| Method (c) | | | | | |
| 6 | | 74 | | 337 | 33,900 |
| 7 | | 66.6 | | 338 | 31,200 |
| 8 | | 75.0 | | 338 | 32,200 |

*with the addition of active carbon
$^1$EA = ethyl acetate

EXAMPLES OF APPLICATIONS

EXAMPLES 9 TO 12

Polyurethane specimens for light-exposure tests were prepared as follows:

a mixture of 92.5 g of a polyol component composed of
  41.9 g of a polyetherol having a hydroxyl number of 29 including approx. 84% of primary hydroxyl groups, obtained by the addition of propylene oxide and ethylene oxide to polypropyleneglycol,
  42.5 g of a polyetherol having a hydroxyl number of 27 including approx. 88% of primary hydroxyl groups, obtained by the addition of propylene oxide and ethylene oxide to trimethylolpropane, and
  8.1 g of 1,4-butanediol,
1.7 g of a 25% w/w solution of 1,4-diazabicyclo[2.2.2]octane in 1,4-butanediol,
0.02 g of dibutyltindilaurate,
0.1 g of a commercial silicon stabilizer,
5.5 g of fluorotrichloromethane and
0.2 g of water was combined with 0.5 g of the heterocyclic amidine derivative of the invention as prepared in Examples 2, 5, 6 and 7 respectively or, for comparison, a prior art amidine,
0.5 g of bis(1,2,2,6,6-pentamethylpiperidyl) sebacate and
0.25 g of an antioxidant mixture comprising 9% w/w of α-tocopherol and 91% w/w of tris(nonylphenyl) phosphite, and then foam-molded with 48.5 g of a prepolymer containing 23% w/w of isocyanate groups and prepared from
  87.2% w/w of 4,4'-diphenylmethane-diisocyanate,
  4.8% w/w of a polyetherol having a hydroxyl number of 250 and obtained by the addition of propylene oxide to propylene glycol, and
  8.0% w/w of dipropylene glycol
to form specimen panels at a temperature of 25° C. (temperature of mold and components of mixture).

The specimens were exposed to light in a Xenotest ® 450 (Hanau) and their degree of discoloration was assessed by comparing the Yellowness Indices (YI) as specified in the *Annual Book of ASTM Standards D 1925-70 (Reapproved 1977)*.

TABLE 2

| Example No. | Stabilizer from Example | YI before exposure | YI after exposure (96h) |
|---|---|---|---|
| *Invention:* | | | |
| 9 | 2 | 1.6 | 16.8 |
| 10 | 5 | 5.0 | 15.8 |
| 11 | 6 | 5.8 | 18.1 |
| 12 | 7 | 4.9 | 17.8 |
| *Comparison:* | | | |
| no stabilizer | | 5.0 | 39.9 |
| open-chain amidine* | | 5.0 | 18.4 |

*compound of the formula

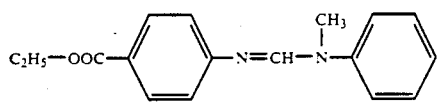

as described in US-A 4,021,471.

We claim:

1. Heterocyclic amidine derivatives of the general formula I

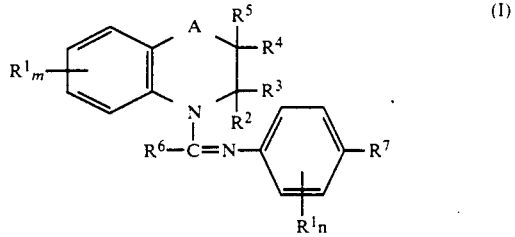

in which the variables

R$^1$ are the same or different and denote hydrogen, C$_1$-C$_4$-alkyl, C$_1$-C$_4$-alkoxy, hydroxyl or chlorine, R$^2$ to R$^5$ denote hydrogen or C$_1$-C$_4$-alkyl and R$^3$ and R$^4$ can together form a five-membered or six-membered ring, R$^6$ denotes hydrogen or C$_1$-C$_8$-alkyl, R$^7$ denotes cyano or —COOR$^8$, —COR$^8$, —CONHR$^8$ or —CONR$^8{}_2$, in which R$^8$ is a straight-chain or branched-chain C$_1$-C$_{12}$-alkyl group which may be interrupted by oxygen atoms, a cyclopentyl or cyclohexyl group or a phenylalkyl group having from 1 to 3 carbon atoms in the alkyl moiety, A is a chemical bond or a methylene group which may additionally carry one or two C$_1$-C$_4$-alkyl radicals, and m and n are each 1 or 2.

2. Heterocyclic amidine derivatives as claimed in claim 1, wherein the variables R$^1$ are the same or different and denote hydrogen, C$_1$-C$_4$-alkyl or C$_1$-C$_4$-alkoxy, R$^6$ denotes hydrogen or C$_1$-C$_3$-alkoxy and R$^7$ denotes cyano or —COOR$^8$.

* * * * *